US008703897B2

(12) United States Patent
Gan et al.

(10) Patent No.: US 8,703,897 B2
(45) Date of Patent: Apr. 22, 2014

(54) POLYURETHANE OLIGOMERS FOR USE IN RESTORATIVE DENTISTRY

(75) Inventors: Seng Neon Gan, Kuala Lumpur (MY); Noor Hayati Binti Abu Kasim, Kuala Lumpur (MY); Fadhel Alsanabana, Kuala Lumpur (MY); Zamri Bin Radzi, Kuala Lumpur (MY); Noor Azlin Binti Yahya, Kuala Lumpur (MY)

(73) Assignee: Universiti Malaya, Kuala Lumpur (MY)

( * ) Notice: Subject to any disclaimer, the term of this patent is extended or adjusted under 35 U.S.C. 154(b) by 0 days.

(21) Appl. No.: 13/377,717

(22) PCT Filed: May 12, 2010

(86) PCT No.: PCT/MY2010/000079
§ 371 (c)(1),
(2), (4) Date: Mar. 5, 2012

(87) PCT Pub. No.: WO2010/143934
PCT Pub. Date: Dec. 16, 2010

(65) Prior Publication Data
US 2012/0271027 A1    Oct. 25, 2012

(30) Foreign Application Priority Data

Jun. 12, 2009 (MY) .............................. PI 20092415

(51) Int. Cl.
*C08G 18/42* (2006.01)
*C08L 91/00* (2006.01)

(52) U.S. Cl.
USPC ........................................ 528/74.5; 525/455

(58) Field of Classification Search
USPC ........................................ 528/74.5; 525/455
See application file for complete search history.

(56) References Cited

U.S. PATENT DOCUMENTS

| 4,791,156 | A | | 12/1988 | Hostettler | |
|---|---|---|---|---|---|
| 4,968,725 | A | * | 11/1990 | Mukai et al. | 522/90 |
| 5,306,798 | A | * | 4/1994 | Horn et al. | 528/58 |
| 5,844,018 | A | * | 12/1998 | Jacobs et al. | 523/116 |
| 6,383,279 | B1 | | 5/2002 | Eckhardt et al. | |
| 6,638,616 | B2 | * | 10/2003 | Tortorello et al. | 428/378 |
| 2005/0059752 | A1 | | 3/2005 | Frances | |

FOREIGN PATENT DOCUMENTS

| CN | 101497684 | 8/2009 |
|---|---|---|
| DE | 10225367 | 9/2003 |
| GB | 1465897 | 3/1977 |
| JP | 2000175941 | 6/2000 |
| WO | 0127181 | 4/2001 |

OTHER PUBLICATIONS

Machine translation of DE 10225367.*
English Abstract of CN101497684.
English Abstract of EP10225367.
English Abstract of JP2000175941.

* cited by examiner

*Primary Examiner* — Mike M Dollinger
(74) *Attorney, Agent, or Firm* — Preston Smirman; Smirman IP Law, PLLC (57) ABSTRACT

A composition of dental filling materials comprising a urethane oligomer obtained from a reaction between natural oil-derived polyols and a diisocyanate in excess to create terminals of isocyanate groups, the oligomer being grafted with an unsaturated acrylic monomer having hydroxyl groups which could react with the isocyanate terminals, and the resulting dental material being curable by free radical initiation.

6 Claims, 6 Drawing Sheets

POLYURETHANE OLIGOMERS FOR USE IN RESTORATIVE DENTISTRY

CROSS-REFERENCE TO RELATED APPLICATION

The instant application claims priority to Malaysian Patent Application No. Pl 20092415, filed Jun. 12, 2009, pending, and PCT International Application No. PCT/MY2010/000079, filed on May 12, 2010, pending, the entire specifications of both of which are expressly incorporated herein by reference.

FIELD OF INVENTION

The present invention relates generally to a composite material for use in dental restoration and a method for producing thereof. In more particular, the present invention relates to a composite material which is made of natural oils-derived polyurethane oligomers and a chemical process of synthesizing the same. The composite material contains unsaturation through incorporating acrylic monomer having hydroxyl group and becomes capable of being cured by light, and is useful for dental applications as restorative composite materials.

BACKGROUND OF THE INVENTION

Amalgam is one of the oldest dental restorative materials which has been used for more than 150 years. Dental amalgam can release minute amounts of elementary mercury, a heavy metal whose toxicity at high intake levels is well-established. People with amalgam filling were found to have higher concentrations of mercury in various tissues including blood, urine, kidney and brain compared to those without. The health of human beings may be affected by the presence of mercury in their body.

As the popularity of dental amalgam has been reduced due to its poor aesthetic value and mercury content, many alternative materials for dental restoration have been developed. These materials include composites, glass ionomers and resin modified glass ionomer cements. They have not been as effective as dental amalgam in providing a durable and long-lasting restoration, especially in larger tooth cavity. Advances in technology have resulted in improvements that have expanded their use.

Dentists have been using a combination of composites and sealants to treat incipient lesions and thereby conserve tooth structure. However, some of the composites may not be appropriate as substitutes for restorations in stress-bearing areas. Some composites that sensitive to moisture and lack of resistance to chewing stress may also compromise their durability.

Glass ionomers are used as dental fillings because they are capable of releasing fluoride and requiring minimal drilling. The procedure of glass ionomers is quick, painless and may not require local anesthesia and the restoration is fairly aesthetic. However, the limitations of this material include low tensile strength, low impact and fracture resistance and degradation qualities. It is not appropriate to be used in the occlusal surfaces of adult teeth and stress-bearing restorations, and situations where moisture control is difficult.

Resin modified glass ionomer cement is a combination of glass ionomer and composite resin. It holds up better than glass ionomer, but not as well as composite resin, and is not recommended for biting surfaces of adult teeth. In general, resin modified glass-ionomer cements can achieve a better aesthetic result than conventional glass ionomers, but not as good as pure composites.

Successful development of resin systems for dental composite should be directed to development of monomers or oligomers which can exhibit the fracture toughness of elastomer-modified resins, while at the same time maintaining a high degree of environmental durability in the oral environment. Sterrett et al (1987) synthesized and evaluated the fracture toughness of a series of urethane toughened methacrylate resin (UTM). The polyol used in formulation of UTM resins serves as both oligomer backbone and urethane soft segment. The structure and functionality of the polyol have a direct effect on the toughness and mechanical properties of the resultant resin. Their result indicated UTM resins based on polyfunctional polyols tend to possess improved toughness. Since then various work has been reported on the development of dental polymer using polyols.

Composite resins has evolved and its refinement has always been focused on the fillers (nano-filler) and its interface, however the matrix system has remained unchanged. The matrix has been predominated by methacrylate-based resin. The common monomers used in resin composite are bisphenol-A glycidyl dimethacrylate (Bis-GMA), urethane dimethacrylate (UDMA) as base monomer or oligomer and triethylene glycol dimethacrylate (TEGDMA) and hydroxyethyl methacrylate (HEMA) as active diluents.

There is a U.K. Patent No. GB1465897 relating to a dental composition. This composition comprises a polymerizable hygienically unsaturated groups and being the reaction product of a urethane polymerize and an ester of acrylic or acrylic acid with a hydroxy Balkan of at least 2 carbon atoms. A Japanese Patent No. JP2000175941 also discloses a repair composition for a denture base which comprises methacrylate, polyurethane, filler and polymerization accelerator. This denture base aims to provide sufficient allowance time for operation, an excellent operability and lessen the refailure of a repair point due to its moderate elasticity.

These methacrylate based resins have a shortcoming in their degree of polymerization being not high enough, and there is also a lack in crosslinking density and thus, compromised their mechanical properties, and increase water uptake and swelling, lead to increase elution of chemicals components. These drawbacks cause poor biocompatibility, reduced of durability and unsatisfied of clinical performance of resin composite restorations.

Numerous studies have been focused on the use of polymeric composites in dental materials. U.S. Pat. No. 6,383,279 also relates to a dental impression composition comprising functionalized polyether derivative bonded through hydroxyl groups of polyether polyol compounds. The level of cyclic oligomeric polyethers is lower than 5.0 wt % and the functionalized polyether derivative contain an aziridino group. This composition provides a poor demouldability of the gypsum model after forming the cast of the impression.

Another U.S. Patent No. US2005059752 relates to a stable, cationically polymerizable dental composition having high filler contents. This composition comprises a compound of UV-and cationically reactive oxirane-functionalized silicone, a filler of silicone oxide, a polymer or copolymer having amine group, a cationic photoinitiator and optionally a photosensitizer.

There is also a dental prosthetic made up of hard, rigid and non-hydrophilic polyurethane (PU) elastomer disclosed in U.S. Pat. No. 4,791,156. The dental prosthetic comprises an organic polyisocyanate, branched chain polyester polyols. It possesses several highly desirable properties such as high heat distortion temperature and excellent impact resistance.

The patented technologies reveal numerous types of dental materials which comprise different types of compositions and synthesized by different methods. These discrepancies will result in a wide variety in the physical and chemical properties of the dental materials synthesized. However, none of the patented technologies provides an environmentally friendly composition of dental materials which possesses both soft segment and hard segments that impart better fatigue resistance and flexural properties. It is therefore desirable for the present invent to provide a composition or a composite resins having natural oils-derived polyurethane oligomers which is capable to overcome the drawbacks of the prior arts, such as the sensitivity to moisture, inappropriacy for stress-bearing areas, shrinkage upon curing, toxicity, low level of toughness and flexural strength and others.

SUMMARY OF INVENTION

The primary object of the present invention is to provide a composition matrix material made of naturally-derived polyurethane oligomers for use in dental restorations.

Another object of the present invention is to innovate a composition dental materials made of polyurethane oligomers derived from natural oil-based polyols, palm oil-based polyols, which possess branches and can increase crosslinking density, thus produce better mechanical strength and dimensional stability.

Still another object of the present invention is to develop a safe and environmentally friendly composite material as an alternative for dental amalgam or filling materials for dental applications.

Yet another object of the present invention is to incorporate certain amounts of natural materials to reduce toxicity and possible allergy reactions of dental materials.

Further object of the present invention is to achieve the required balance in product properties yet provide a product of dental materials with reasonable and competitive cost.

At least one of the preceding objects is met, in whole or in part, by the present invention, in which one of the embodiments of the present invention describes a composition of dental filling materials comprising a urethane oligomer obtained from a reaction between natural oil-derived polyols and a diisocyanate, the oligomer being grafted with an unsaturated acrylic monomer having hydroxyl groups and being curable by free radical initiation.

Preferably, the urethane oligomer comprises polyol and diisocyanate in a ratio of 1:2 to 1:3 by weight of the oligomer.

One of the preferred embodiments of the present invention discloses that the polyols are derived from palm oils, coconut oils, soy oils, linseed oils, castor oils, rapeseed oils, tallow oils, fish oils or a combination of any two or more thereof.

In another preferred embodiment of the present invention, the polyols are glycerol, ethylene glycol, 1,4-butandiol or a combination of any two or more thereof.

Still another preferred embodiment of the present invention is composition of dental materials with a diisocyanate which can be methyl diphenyl diisocyanate (MDI), toluene diisocyanate (TDI), hexamethylene diisocyanate (HDI) or a combination of any two or more thereof.

Preferably, the unsaturated acrylic monomer is hydroxymethacrylate, hydroxyethyl acrylate (HEA), hydroxyethylmethacrylate (HEMA), acrylic acid, methacrylic acid, pentaerythritol tri/tetraacrylate (PETA), trimethylolpropane triacrylate (TMPTA), hexamethylene diacrylate (HDDA), 2-hydroxyethyl acrylate (2-HEA), 2-hydroxypropyl acrylate (2-HPA), 2-hydroxy acrylate (2-HBA), isobonyl acrylate (IBOA) or a combination of any two or more thereof.

Yet another preferred embodiment of the present invention discloses that the free radical initiator is an azo compound, an organic peroxide, hydroquinone, p-methoxyphenol, nitrobenzene or 2,6-di-tetra-butyl-4-methylphenol (BHT). Preferably, the free radical initiation is activated by light.

The composition of dental materials invented is a matrix system or resins which can be used in formulating dental restorative materials. This safe and environmentally friendly composition is able to specifically replace the toxic mercury amalgam dental filing materials.

One skilled in the art will readily appreciate that the present invention is well adapted to carry out the objects and obtain the ends and advantages mentioned, as well as those inherent therein. The embodiments described herein are not intended as limitations on the scope of the invention.

BRIEF DESCRIPTION OF THE DRAWINGS

For the purpose of facilitating an understanding of the invention, there is illustrated in the accompanying drawing the preferred embodiments from an inspection of which when considered in connection with the following description, the invention, its construction and operation and many of its advantages would be readily understood and appreciated.

DETAILED DESCRIPTION OF THE INVENTION

The present invention relates generally to a composite material for use in dental restoration and a method for producing thereof. In more particular, the present invention relates to a composite material which is made of natural oils-derived polyurethane oligomers and a chemical process of synthesizing the same. The composite material is useful for dental applications as restorative composite materials.

Hereinafter, the invention shall be described according to the preferred embodiments of the present invention and by referring to the accompanying description and drawings. However, it is to be understood that limiting the description to the preferred embodiments of the invention and to the drawings is merely to facilitate discussion of the present invention and it is envisioned that those skilled in the art may devise various modifications without departing from the scope of the appended claim.

The present invention discloses a composition of dental filling materials comprising a urethane oligomer obtained from a reaction between natural oil-derived polyols and a diisocyanate, the oligomer being grafted with an unsaturated acrylic monomer having hydroxyl groups and being curable by free radical initiation.

In the present invention, a composition of branched macromer with polyfunctionality is developed to produce a high crosslinked density, which increase its mechanical properties. One of the preferred embodiments of the present invention discloses that the polyols are derived from natural oils such as palm oils, coconut oils, soy oils, linseed oils, castor oils, rapeseed oils, tallow oils, fish oils or a combination of any two or more thereof. Most preferably, the palm oil-based polyols are used in the present invention. The use of palm oil-based polyol is also capable of enhancing the biocompatibility of the composition synthesized. In accordance with another preferred embodiment of the present invention, the types of According to the preferred embodiment of the present invention, the unsaturated acrylic monomer which can be applied include hydroxymethacrylate, acrylic acid, methacrylic acid, PETA, TMPTA, HDDA, 2-HEA, 2-HPA, 2-HBA, IBOA or a combination of any two or more thereof. In the present invention, hydroxymethacrylate is most preferably used monomer to produce a composition of polyurethane with acrylate terminal (having C=C group).

Any excess reagents such as the excess diisocyanate or the acrylic monomer can be removed by solvent extraction and distillation. The final compound would be a polyfunctional molecule with two or more —C=C— groups. An example of such a structure is shown below.

polyols employed can be glycerol, ethylene glycol, 1,4-butandiol or a combination of any two or more thereof.

Palm oil-based polyols have more than 2 functional groups, causing the polymer branched and could have higher crosslinking density and three dimensional linked structure to produce better mechanical strength and dimensional stability. According to one of the preferred embodiments of the present invention, the composition invented possesses both soft segment and hard segments which could impart better fatigue resistance and flexural properties in the dental filing materials produced.

Still another preferred embodiment of the present invention is composition of dental materials with a diisocyanate which can be methyl diphenyl diisocyanate (MDI), toluene diisocyanate (TDI), hexamethylene diisocyanate (HDI) or a combination of any two or more thereof. Most preferably, MDI is applied as the diisocyanate compound in the present invention. The composition or the macromer is synthesized by reacting palm oil polyols with excess amount of diisocyanate to produce a prepolymer with isocyanate (—CNO) terminals. Preferably, the polyols and the diisocyanate are reacted in a ratio of 1:2 to 1:3 by weight of the composition. Most preferably, the polyols and the diisocyanate are reacted in a ratio of 1:2 to 1:2.2 by equivalent weights of the composition, in order to convert the hydroxyl (—OH) to isocyanate (—NCO). Subsequently, an hydroxyl terminated acrylic monomer, such as HEMA, can be immediately added. Addition of the unsaturated acrylic monomers having hydroxyl groups is capable of leading to the grafting of the these monomers onto the oligomers through the reaction of hydroxyl with the isocyanate. Generally, the acrylic monomer is grafted according to the following equation:

The polymerization or curing of the composition is initiated by free radical initiators or free radical catalysts. Free radical initiators are compounds that is capable of producing radical species to start radical polymerization reactions. These substances generally possess weak bonds that have low bond dissociation energies. Typical examples of the free radical initiators are azo compounds and peroxides. Examples of azo compounds that are preferably used includes bis-azoisobutyronitrile (AIBN) and bis-azocyclohexanecarbonitril (ABCN); whereas di-t(tertiary)-butylperoxide (tBuOOtBu) and benzoyl peroxide are the preferred organic peroxides used. Besides the azo compounds and organic peroxides, other free radical initiator such as hydroquinone, p-methoxyphenol, nitrobenzene or BHT can also be applied according to another preferred embodiment of the present invention. The initiator may be used in an effective amount, preferably in an amount of 100 to 1000 ppm.

The polymerization by free radical initiation can be activated by chemical or external energy, such as light or heat. Preferably, the free radical initiation of the present invention is activated by visible light. The composition is cured by the free radical initiators upon activation by visible light during the restoration process.

The palm-oil-based restorative dental materials invented possess good properties comparable to some established commercial products. A series of evaluation tests have been conducted on the composition (BP-UDMA macromer) invented, including characterization of the BU-DMA macromer and the BU-DMA-based composite. Illustrated in FIG. 1 to FIG. 5 are the properties of the BU-DMA macromer in comparison to various commercially obtained resins.

Figure 1:
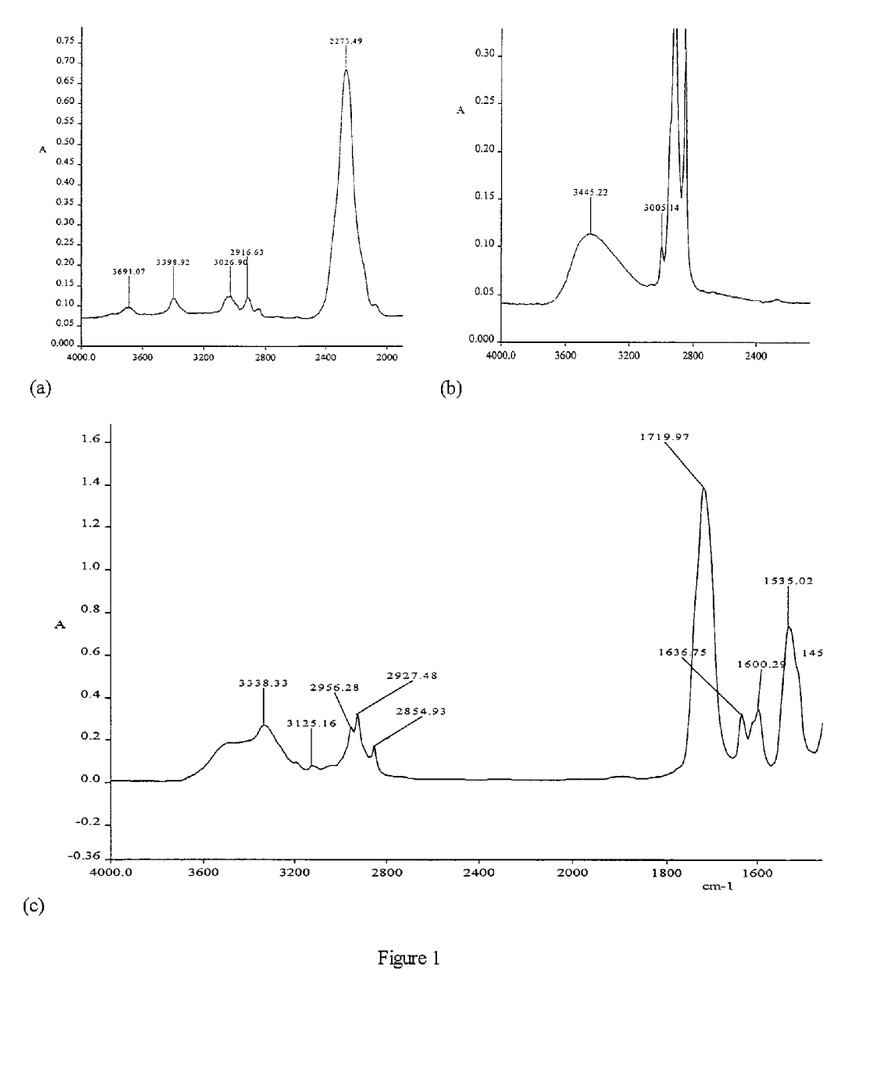
FIG. 1 is a Fourier Transform Infra Red (FTIR) spectrum of the MDI (a), the natural-oil based biopolyol (b), and the biopolyol-urethane dimethacrylate (BP-UDMA) macromer (c), one of the examples of the macromers produced according to the method described in one of the preferred embodiments of the present invention; showing the major characteristic peaks reading (A) at each peak including adsorption peaks of free isocyanate (—NCO—) and the formation of urethane (—NH—).

As shown in FIG. 1, the chemical structure of BP-UDMA, one of the examples of the macromers as embodied in the present invention can be identified by FTIR spectrum. The spectrum of FIG. 1(c) shows the characteristic carbonyl absorption peaks at 1737 cm$^{-1}$, —N—H stretching vibration at 3365 cm$^{-1}$, and bending and stretching vibration at the —C=CH— peaks at 947 and 1633 cm$^{-1}$. Moreover, the BP-UDMA spectrum reveals that all isocyanate have been reacted by showing disappearance or absence of 2270 cm$^{-1}$ peak characteristic of isocyanate (—NCO—), which was present in the starting material, in FIG. 1(a), and the disappearance of the hydroxyl groups of polyol at 3445 cm$^{-1}$, which was present in the polyol in FIG. 1(b), and HEMA, and substituted by the appearance of urethane —N—H at 3365 cm$^{-1}$.

Figure 2:
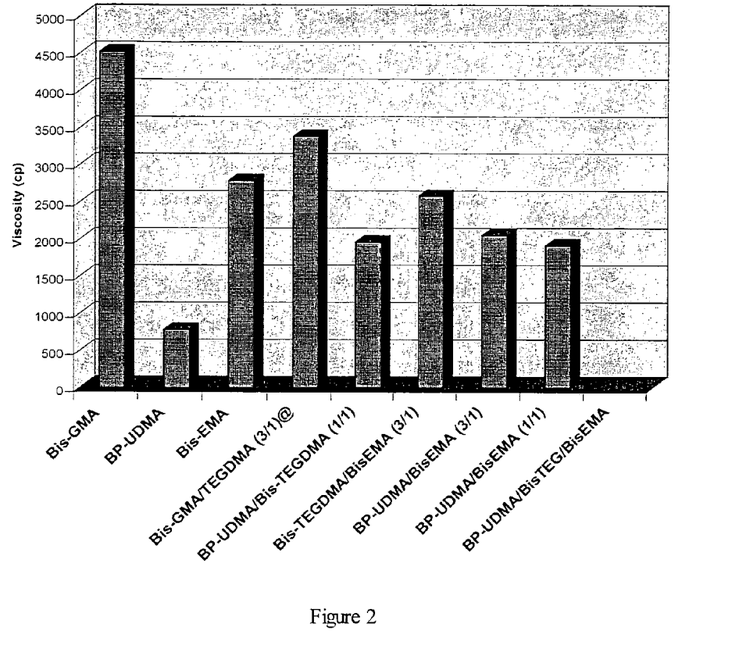
FIG. 2 is a viscosity bar chart of showing a comparison of viscosities among various types of commercial resins in comparison to the BP-UDMA macromer invented and its mixture with other resins.

A comparison of viscosities among various types of commercial resins including the BP-UDMA macromer and its mixture with some commons monomers is shown in FIG. 2. The BP-UDMA macromer synthesized gives a much lower viscosity compared to the commonly used methacrylate-based composite for dental applications, such as Bis-GMA. The BP-UDMA macromer is completely miscible with a number of common unsaturated monomers. For instance, when BP-UDMA is blended Bis-EMA at 1:1 ratio, it could produce a medium viscosity between 2000 cp to 3000 cp, which permits the increase of filler to produce composite with easier handling. In addition, BP-UDMA can blend well with other commercial monomers, photo-initiators and silanated glass filler during the preparation of mixed resin and composites.

Figure 3:
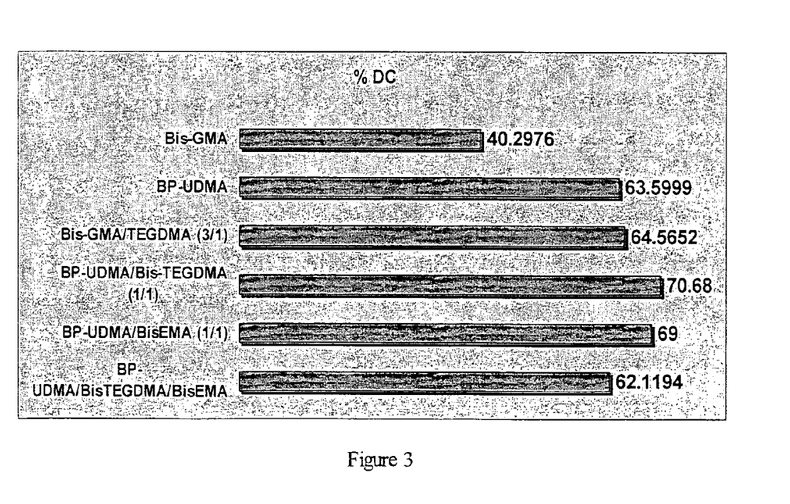
FIG. 3 is a bar chart showing a comparison of the degree of conversion (% DC) among various types of commercial resins in comparison to the BP-UDMA macromer invented and its mixture with other resins.

Besides, the BP-UDMA also possesses a higher degree of conversion and cross-linking density compared to the Bis-GMA, as illustrated in FIG. 3. The degree of conversion (% DC) of each specimen is determined by comparison of the ratio of the aliphatic carbon-carbon double bond (C=C) with that of the aromatic component for the cured and uncured states. As shown in FIG. 3, the % DC of neat Bis-GMA is very low compared to BP-UDMA, due to the very high viscosity of Bis-GMA. Consequently, the Bis-GMA tends to have unreacted monomer, which could be a health hazard. The BP-UDMA invented is therefore a healthier product to be used in dental applications. Furthermore, the BP-UDMA is also capable of achieving an increased degree of conversion and cross-linking when it is blended with other macromers as a resin system.

Figure 4:
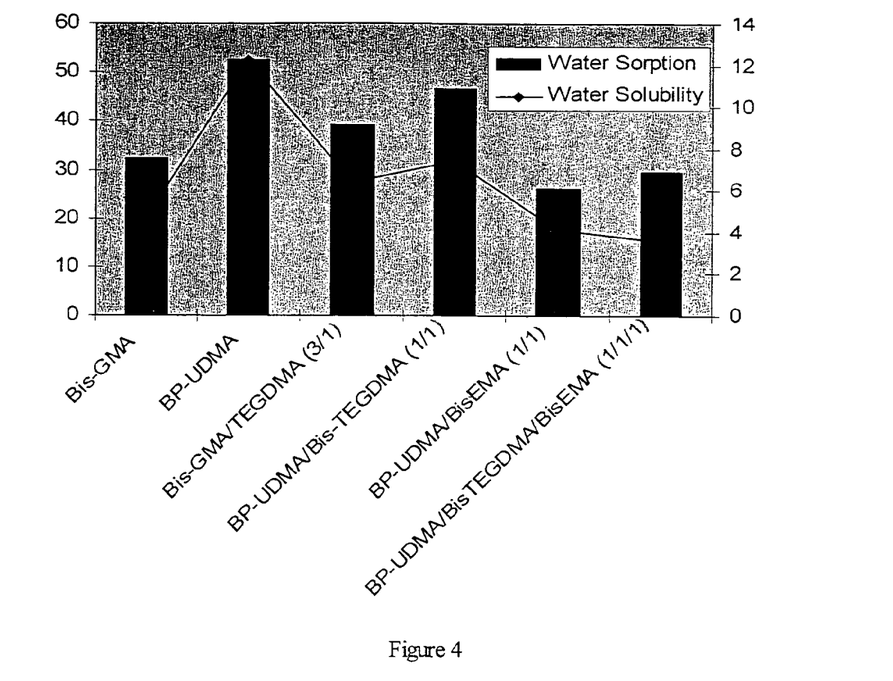
FIG. 4 shows a comparison of water sorption and water solubility mean among various types of commercial resins in comparison to the BP-UDMA macromer invented and its mixture with other resins.

FIG. 4 shows the comparison of water sorption and solubility mean values among various types of commercial resins including the BP-UDMA macromer and its mixture with other resins. Pure BP-UDMA is capable of achieving a water sorption range of 50 µg/mm$^2$ to 55 µg/mm$^2$, and a water solubility of 10.5 µg/mm$^2$ to 14.0 µg/mm$^2$. When it is combined with other resins comprising the hydrophobic Bis-EMA, to form BP-UDMA/BisEMA or BP-UDMA/Bis-TEGDMA/BisEMA, the water sorptions and solubilities can better than the current commercial resins, such as Bis-GMA/TEGDMA.

Figure 5:
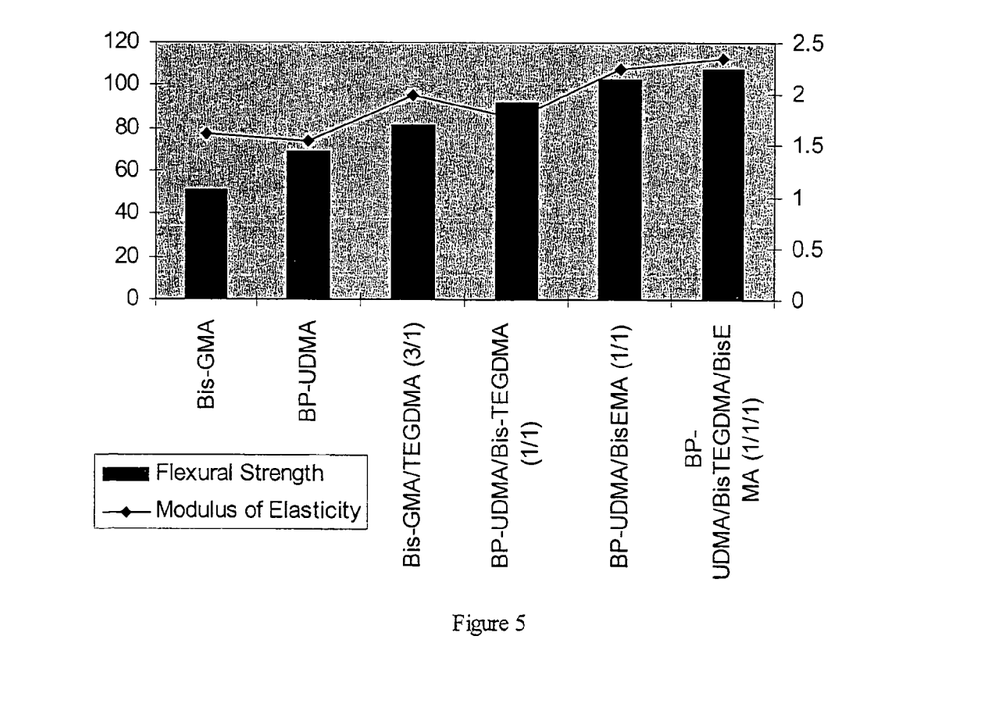
FIG. 5 shows the comparison of flexural strength and flexural modulus among various types of commercial resins in comparison to the BP-UDMA macromer invented and its mixture with other resins.

As set forth in the preceding description, the composition of the present invention is capable of imparting better fatigue resistance and flexural properties in the dental filling materials. It is shown in FIG. 5 that the flexural strength of the pure BP-UDMA is in a range of 62.8 to 75.4 MPa with a flex modulus range of 1.4 to 1.7 Gpa. Likewise, when the BP-UDMA is combined with other resins, higher flexural strength and modulus can also be shown. For example, BP-UDMA/Bis-TEG can absorb twice the amount of energy than Bis/TEG to fracture.

Figure 6:
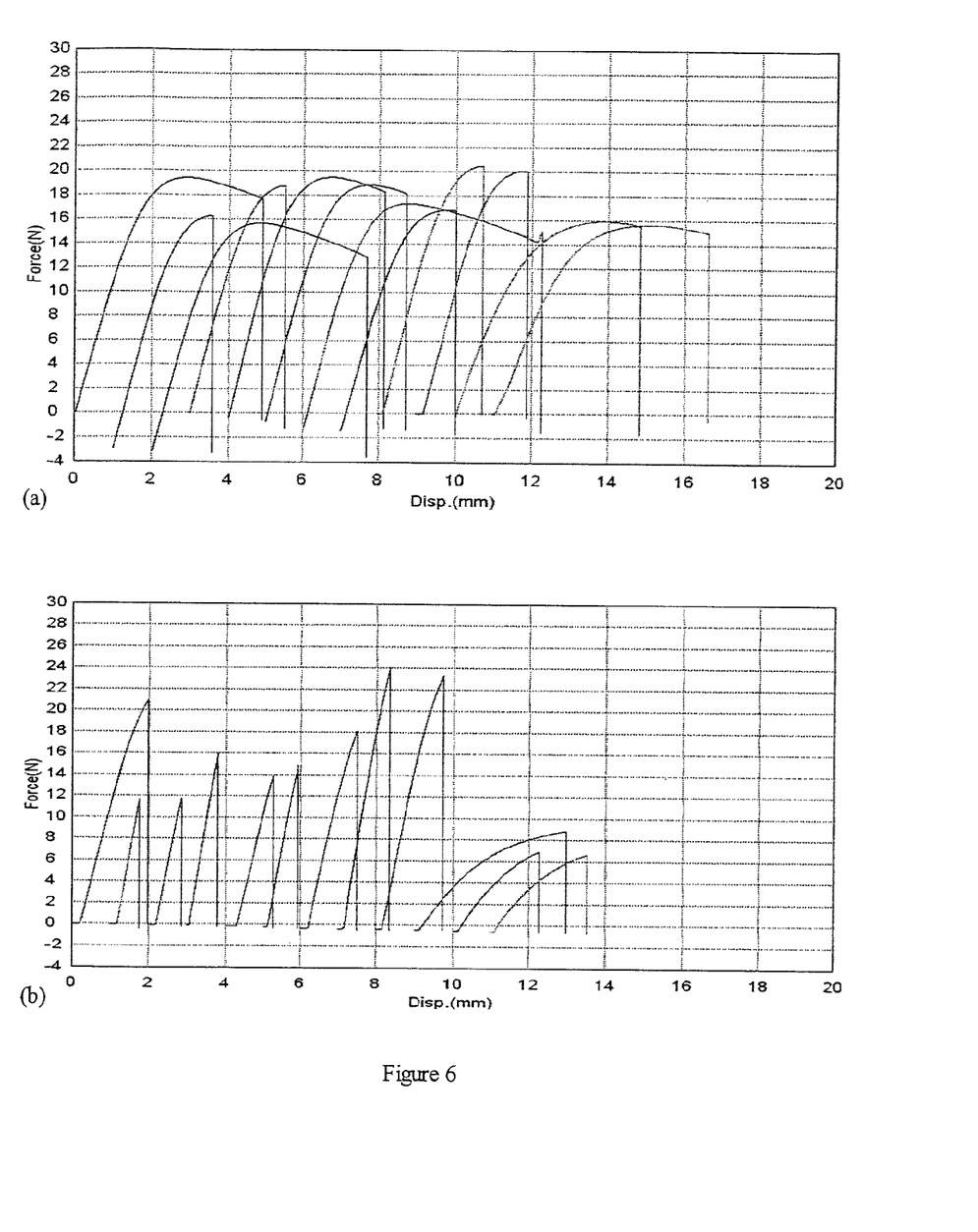
FIG. 6 is the stress/strain curve showing the toughness of the BU-UDMA (a) and the brittleness of the commercially available Bis-GMA (b).

Apart from these, the BP-UDMA invented possesses a higher toughness compared to Bis-GMA. This is proven by the larger area below the stress/strain deflection shown in FIG. 6(a), which refers to BP-UDMA, compared to FIG. 6(b), which refers to Bis-GMA. In another example, the BP-UDMA/Bis-TEG exhibits significantly higher toughness than Bis/TEG significantly. The sample can therefore absorb twice the amount of energy than Bis/TEG to fracture.

Figure 7:
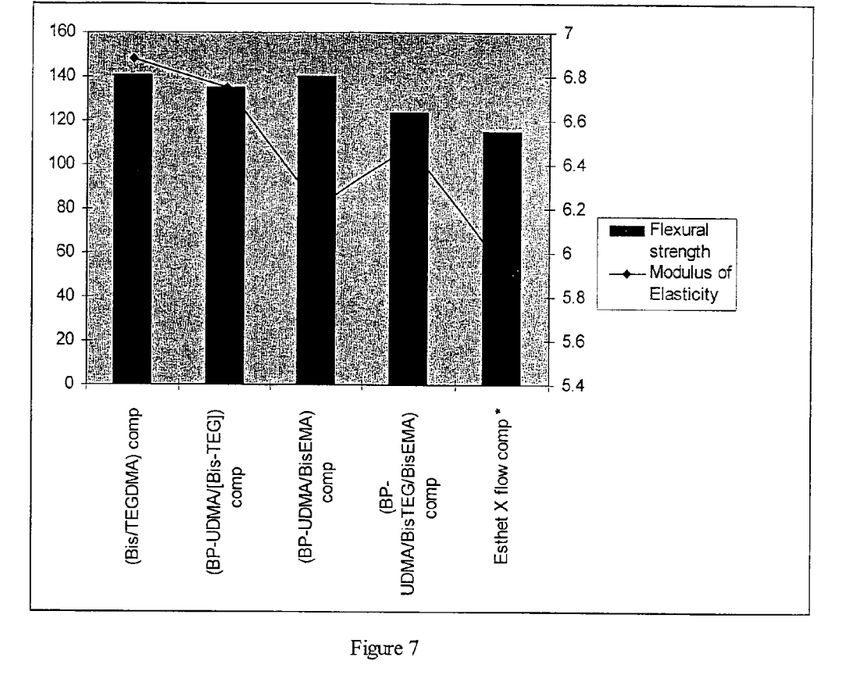
FIG. 7 shows the comparison of flexural strength and flexural modulus among various types of commercial composites and BU-UDMA-based composites as described in one of the preferred embodiment of the present invention.

The BP-UDMA can be combined with other types of resins to form composite. The composite can be prepared by blending the monomers mixtures (resin) with 60% by weight of silanated barium borosilica glass filler, which increase the physical properties of resin. As shown in FIG. 7, the flexural strength of experimental composites based on BP-UDMA-based composite are comparable to the experimental common composite based on Bis-TEG and commercial Esthet X. flow.

Figure 8:
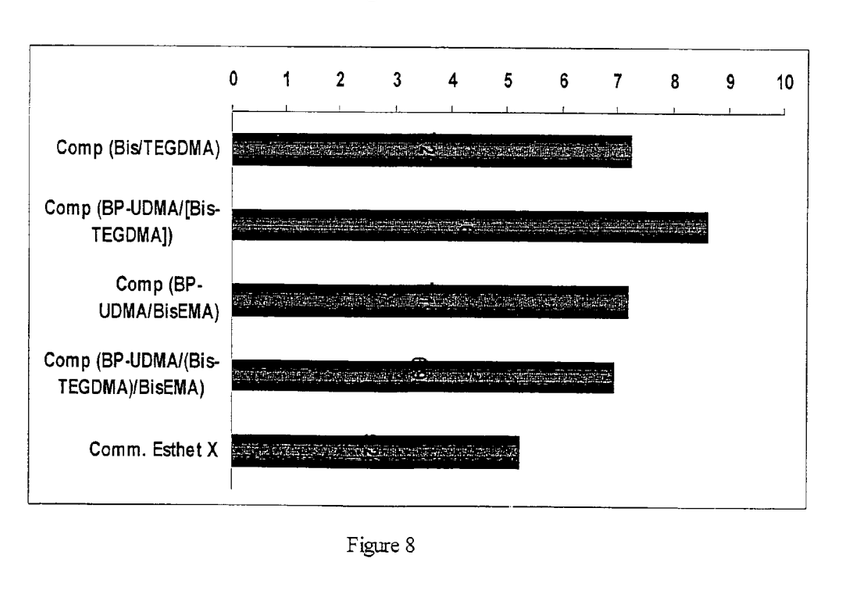
FIG. 8 shows the comparison of water sorption among various types of commercial composites and BU-UDMA-based composites.

Besides enhancing the flexural strength and flexural modulus value, water absorption of the composite of BP-UDMA can also be increased. As shown in FIG. 8, the water sorption of experimental composites based on BP-UDMA resin are also comparable to the experimental common composite based on Bis-TEG and commercial Esthet X. flow.

Figure 9:
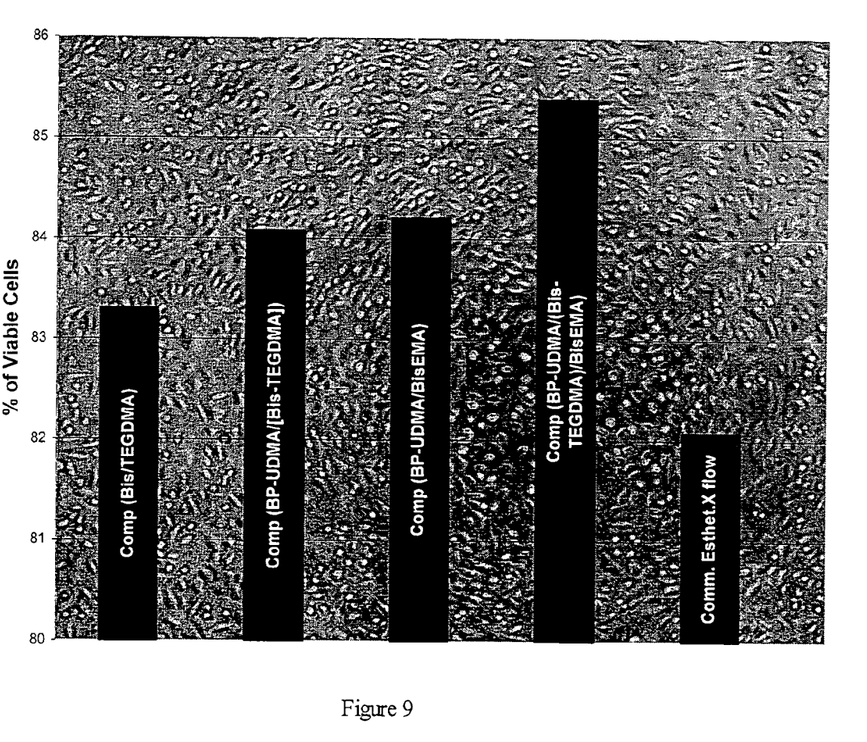
FIG. 9 is a cytotoxicity bar chart showing the comparison of cytotoxicity among various types of commercial composites and BU-UDMA-based composites.

The composition of the present invention also reveals low cytotoxicity. FIG. 9 is a cytotoxicity bar chart showing the comparison of cytotoxicity among various types of BP-UDMA-based composite. The re-inforcement of the composite by using the composition invented is able to increase the percentage of viable cell. The entire experimental composites based on BP-UDMA showed non toxic, because the high degree of conversion of BP-UDMA resins lead to lower the elution free monomers, which affect the biocompatibility.

The present disclosure includes as contained in the appended claims, as well as that of the foregoing description. Although this invention has been described in its preferred form with a degree of particularity, it is understood that the present disclosure of the preferred form has been made only by way of example and that numerous changes in the details of construction and the combination and arrangements of parts may be resorted to without departing from the scope of the invention.

EXAMPLE

Examples are provided below to illustrate different aspects and embodiments of the present invention. These examples are not intended in any way to limit the disclosed invention, which is limited only by the claims.

Example 1

The composition of materials used for making one of this biopol is given in Table 1.

TABLE 1

| Material | Weight/g |
| --- | --- |
| Oleic acid | 1840.0 |
| Phthalic anhydride | 412.0 |
| Glycerol | 580.0 |

Glycerol and phthalic anhydride were placed into the reaction flask fitted with a Dean and Stark tube and a stirrer. The mixture was stirred at 150-250 rpm and heated at 80-110° C. for about 2 hours, until all the phthalic anhydride has dissolved into the glycerol and reacted to form half ester, without evolution of water. Oleic acid was then added and the temperature raised gradually to 180-210° C. over 2 hours and maintained at 210-220° C. The water generated was collected at the decanter arm. The reaction has approached completion when the total amount of water collected was around 97 g and the acid value has dropped below 5 mgKOH g$^{-1}$. The product is a non-vicious light yellowish liquid with a hydroxyl value of around 134 mgKOH g$^{-1}$.

A plausible structure of the biopol described in Example 1 is as shown below:

where R—COO side chain is formed from the oleic acid. Each molecule would contain two or more hydroxyl (—OH) group. This structure is subsequently represented as follow:

Example 2

The process to produce one of the BP-UMA comprises of (i) reacting excess amount of diisocyanate with polyol to provide a polyurethane prepolymer, containing terminal —CNO and (ii) reacting the polyurethane prepolymer with an acrylic monomer having a hydroxyl group such as HEMA to provide BP-UDMA. 50 g of MDI was first poured into 500-ml rounded flask and was purged with nitrogen for 5 mints to expel any moisture in the air of the flask. The flask then was heated to 60° C., under constant moderate stirring (100-200 rpm), using mechanical stirrer. 26 g of palm oil-based polyol (as described in Example 1) was added to the MDI drop-wise using dropper under nitrogen atmosphere, and the mixture was stirred for another 30 mints after all of the polyol had been added into the MDI. The mixture was cooled down to 10° C. using an ice bath, and 90 g of HEMA, which was already mixed with 0.1 g of hydroquinone and 0.05 g of dibutyl tin dilurate (a urethane catalyst), was added into the reactor drop-wise over 30-45 minutes, at stirring speed of around 160 rpm. The mixture was stirred for 2 hrs under nitrogen blank. FTIR can be used to monitor the progress of the formation of BP-UDMA, from the disappearance of the —NCO peak at 2270 cm$^{-1}$. Finally, the BP-UDMA was poured pouring in brown glass container and stored in refrigerator for future use.

The formation of polyurethane prepolymer, containing terminal —CNO can be represented as follow:

The above structure can be represented as follow:

The reaction of the isocyanate terminated prepolymer with HEMA, $H_2C=C(CH_3)COOCH_2CH_2OH$, can be represented as follow:

Where the structure of HEMA is

Example 3

With the aim to characterize the BP-UDMA monomer and investigate its application for dental resin and composite, the experimental visible light cured samples (monomers, resins, and composites) were prepared, using the commercial materials showed in table 2.

TABLE 2

| Component | Chemical nomenclature | Acronym | Sources |
| --- | --- | --- | --- |
| Base monomer | Bis-GMA (2,2-bis[4-(2-hydroxy-3-methacryloxyprop-1-oxy)phenyl]propane) | Bis-GMA | Essington, Pennsylvania, USA |
| | Ethoxylated bisphenol A dimethacrylate | Bis-EMA | Essington, Pennsylvania, USA |
| | Urethane dimethacrylate | UDMA | Essington, Pennsylvania, USA |

TABLE 2-continued

| Component | Chemical nomenclature | Acronym | Sources |
| --- | --- | --- | --- |
| Diluent monomer | Hydroxyethyl methacrylate | HEMA | Sigma-Aldrich |
| | triethylene glycol dimethacrylate | TEGDMA | Essington, Pennsylvania, USA. |
| Photoinitiator system | Camphorquinone | CQ | Sigma-Aldrich |
| | Ethyl-4-N,N-dimethylaminobenzoate | 4E | Sigma-Aldrich |
| Filler | Barium Borosilicate glass | | Essington, Pennsylvania, USA |
| Esthet. X flowable composite | | | Dentsply, Kurrary |

The unfilled visible light curable samples contain one monomer or a mixture of 2 more monomers (resin) without filler. The weight percentages of monomers and photo-initiators (0.2% CQ and 0.8 4E, which is the common % by weight) were calculated and weighed, as in Table 3. They were mixed homogenously in glass container using a plastic spatula. Then mixtures were kept in light protected glass containers. For filled visible light curable sample, the same procedure was employed, except the filler, a silanated barium glass filler was added to the resin mixture at 60% by weight. This was achieved by gradually adding the filler into the resin over a period of 30 min in a glass container and mixed homogeneously by using a plastic spetula. The composite material was then degassed under vacuum (30° C.) overnight.

Example 4

From each visible light cured sample (monomers or resins or composites), about 0.6 ml was transferred to a 10 ml disposable syringes, and the tip was connect to the vacuum pipe for a few hrs (especially composite sample) to eliminate any trapped air. The plastic syringe was used as delivery device for dispensing the light curable sample into the mold (or oral cavity). Generally, the preparation procedure was performed at room temperature (23-24° C.) under yellow light to avoid photo initiation or unintentional polymerization by ambient light. Each syringe was filled with sample and wrapped with balked tap and coded according to the label on the glass container as in Table 3, and stored in refrigerator until used or required.

TABLE 3

| Samples | Samples composition by weight % of materials | | | | |
|---|---|---|---|---|---|
| | Bis-GMA | BP-UDMA | Bis-EMA | TEGDMA | Filler |
| Bis-GMA* | 99% | | | | |
| BP-UDMA | | 99% | | | |
| Bis-GMA/TEGDMA (3/1)** | 74.25% | | | 24.75% | |
| BP-UDMA/Bis-TEGDMA (1/1) | 36.75% | 49.5% | | 12.25% | |
| BP-UDMA/BisEMA (1/1) | | 49.5% | 49.5% | | |
| BP-UDMA/BisTEGDMA/BisEMA (1/1/1) | 24.75% | 33% | 33% | 8.25% | |
| (Bis/TEGDMA) comp*** | 29.25% | | | 9.75% | Y |
| (BP-UDMA/[Bis-TEG]) comp | 24.99% | 33.33% | 33.33% | 8.32% | Y |
| (BP-UDMA/BisEMA) comp | | 19.5% | 19.5% | | Y |
| (BP-UDMA/BisTEG/BisEMA) comp | 9.75% | 13 | 13 | 3.25% | Y |

Note:
The Camphorquinone (CQ) and Ethyl-4-N,N-dimethylaminobenzoate (4E) weight % were 0.2% and 0.8, respectively, for each sample.
*Bis-GMA: was used as a control group for visible light cur momoer.
**Bis-GMA/TEGDMA: (common dental resin) was used as a control group for visible light cure resin.
***(Bis/TEGDMA) comp: (based on common dental resin) was used as a control group for visible light cur composite.
Y = filled incorporated at 60% wt of the resin.

The invention claimed is:

1. A composition of dental filling materials, comprising:
a urethane oligomer having isocyanate terminals obtained from a reaction between natural oil-derived polyols and an excess diisocyanate, wherein the oligomer being grafted with an unsaturated acrylic monomer having hydroxyl groups forming a prepolymer with unsaturated terminals being curable by free radical initiators wherein the natural oil-derived polyol is a reaction product of the oleic acid, phthalic anhydride and glycerol, and wherein the composition further comprises a polyfunctional acrylate monomer comprising 2,2-bis[4-(2-hydroxy-3-methacryloxyprop-1-oxy)phenyl]propane, ethoxylated bisphenol A dimethacrylate, triethylene glycol dimethacrylate, or mixtures thereof.

2. The composition according to claim 1, wherein the natural derived polyols are derived, in addition to the oleic acid, from the group consisting of palm oils, coconut oils, soy oils, linseed oils, castor oils, rapeseed oils, tallow oils, fish oils, and combinations thereof.

3. The composition according to claim 1, wherein the diisocyanate is selected from the group consisting of methyl diphenyl diisocyanate, toluene diisocyanate, hexamethylene diisocyanate, and combinations thereof.

4. The composition according to claim 1, wherein the unsaturated acrylic monomer further comprises a monomer is selected from the group consisting of hydroxymethacrylate, hydroxyethyl acrylate (HEA), hydroxyethylmethacrylate (HEMA), acrylic acid, methacrylic acid, pentaerythritol tri/tetraacrylate (PETA), trimethylolpropane triacrylate (TMPTA), hexamethylene diacrylate (HDDA), 2-hydroxyethyl acrylate (2-HEA), 2-hydroxypropyl acrylate (2-HPA), 2-hydroxy acrylate (2-HBA), isobornyl acrylate (IBOA), and combinations thereof.

5. The composition according to claim 1, wherein the free radical initiator is selected from the group consisting of an azo compound, an organic peroxide, hydroquinone, p-methoxyphenol, nitrobenzene, 2,6-di-tetra-butyl-4-methylphenol, and combinations thereof.

6. The composition according to claim 1, wherein the composition comprises a soft segment and a hard segment for providing better fatigue resistance and flexural properties to the dental filing materials.

* * * * *